US010589068B2

United States Patent
Lampropoulos et al.

(10) Patent No.: US 10,589,068 B2
(45) Date of Patent: Mar. 17, 2020

(54) CORONARY ACCESS AND DELIVERY SYSTEMS

(71) Applicant: Merit Medical Systems, Inc., South Jordan, UT (US)

(72) Inventors: Fred Lampropoulos, Salt Lake City, UT (US); Matt Toone, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 56 days.

(21) Appl. No.: 15/459,183

(22) Filed: Mar. 15, 2017

(65) Prior Publication Data

US 2017/0266415 A1    Sep. 21, 2017

Related U.S. Application Data

(60) Provisional application No. 62/309,209, filed on Mar. 16, 2016.

(51) Int. Cl.
| | | |
|---|---|---|
| A61M 25/06 | (2006.01) | |
| A61M 25/00 | (2006.01) | |
| A61B 17/34 | (2006.01) | |
| A61M 25/01 | (2006.01) | |
| A61N 1/05 | (2006.01) | |
| A61B 17/00 | (2006.01) | |

(52) U.S. Cl.
CPC ..... *A61M 25/0662* (2013.01); *A61B 17/3468* (2013.01); *A61M 25/0041* (2013.01); *A61M 25/0102* (2013.01); *A61N 1/056* (2013.01); *A61N 1/0563* (2013.01); *A61B 2017/00243* (2013.01); *A61M 25/005* (2013.01); *A61M 2025/0681* (2013.01); *A61N 2001/0585* (2013.01)

(58) Field of Classification Search
CPC ............. A61N 1/056; A61N 1/0563; A61N 2001/0585; A61B 2017/00243; A61B 17/24; A61M 25/0102; A61M 25/0662; A61M 2025/0681; A61M 25/01
See application file for complete search history.

(56) References Cited

U.S. PATENT DOCUMENTS

| | | | |
|---|---|---|---|
| 4,976,691 | A | 12/1990 | Sahota |
| 5,267,982 | A | 12/1993 | Slyvanowicz |
| 5,445,625 | A | 8/1995 | Voda |
| 6,277,107 | B1 | 8/2001 | Lurie et al. |
| 6,458,107 | B1 | 10/2002 | Ockuly |
| 6,638,268 | B2 | 10/2003 | Naizi |

(Continued)

OTHER PUBLICATIONS

International Search Report and Written Opinion dated Jun. 7, 2017 for PCT/US2017/022420.

(Continued)

*Primary Examiner* — George J Ulsh
(74) *Attorney, Agent, or Firm* — Stoel Rives LLP

(57) ABSTRACT

Coronary access and delivery systems are provided. A coronary access system can include a coronary sinus guide and a first core. A lateral vein delivery system can include a lateral vein introducer and a second core. The coronary sinus guide, the lateral vein introducer, and the first and second cores may be designed or shaped to access a predetermined position within a heart of a subject. For example, the coronary sinus guide, the lateral vein introducer, and/or the first and second cores can be used in combination to access the predetermined position within the heart of the subject.

21 Claims, 14 Drawing Sheets

(56) References Cited

U.S. PATENT DOCUMENTS

| | | |
|---|---|---|
| 6,966,896 B2 | 11/2005 | Kurth et al. |
| D533,270 S | 12/2006 | Kierce |
| 7,384,422 B2 | 6/2008 | Worley et al. |
| 7,462,184 B2 | 12/2008 | Worley et al. |
| 7,993,351 B2 | 8/2011 | Worley et al. |
| D669,168 S | 10/2012 | Krueger et al. |
| D674,082 S | 1/2013 | Efinger |
| D710,495 S | 8/2014 | Wu et al. |
| D713,027 S | 9/2014 | Adams |
| D724,725 S | 3/2015 | Chang |
| D726,304 S | 4/2015 | Yatabe et al. |
| 9,033,996 B1 | 5/2015 | West |
| D746,445 S | 12/2015 | Lazarus |
| D751,196 S | 3/2016 | Wapler |
| D752,213 S | 3/2016 | Paul |
| D755,368 S | 5/2016 | Efinger |
| D776,259 S | 1/2017 | Eldredge |
| 2006/0259111 A1 | 11/2006 | Peterson et al. |
| 2014/0025041 A1 | 1/2014 | Fukuoka et al. |

OTHER PUBLICATIONS

Notice of Allowance dated May 8, 2019 for U.S. Appl. No. 29/644,791.
European Search Report dated Oct. 1, 2019 for EP17767387.8.

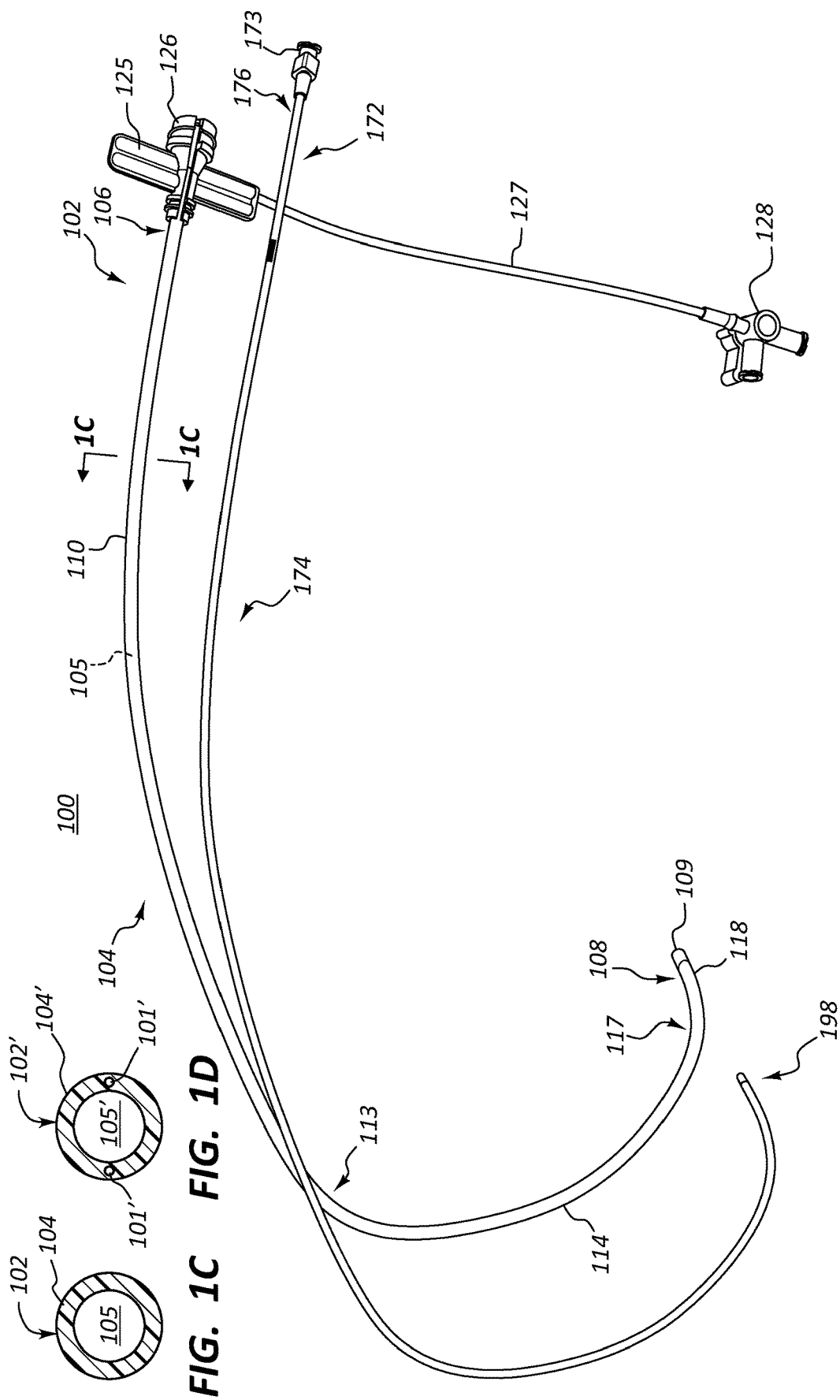

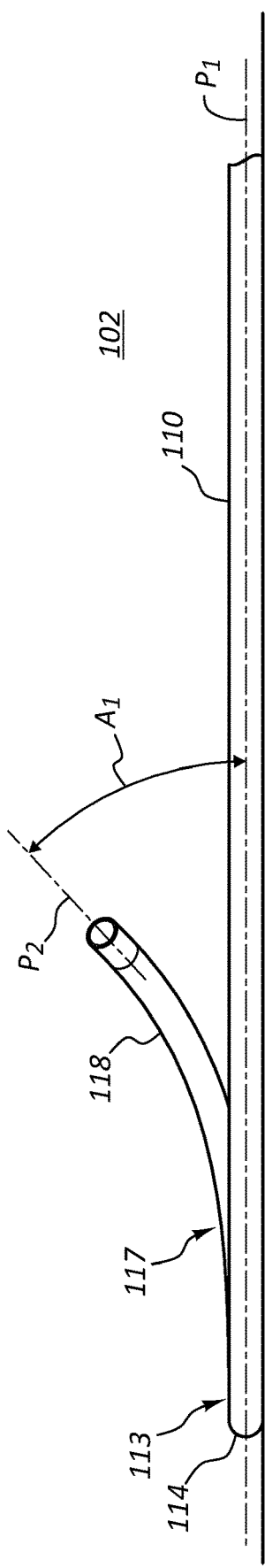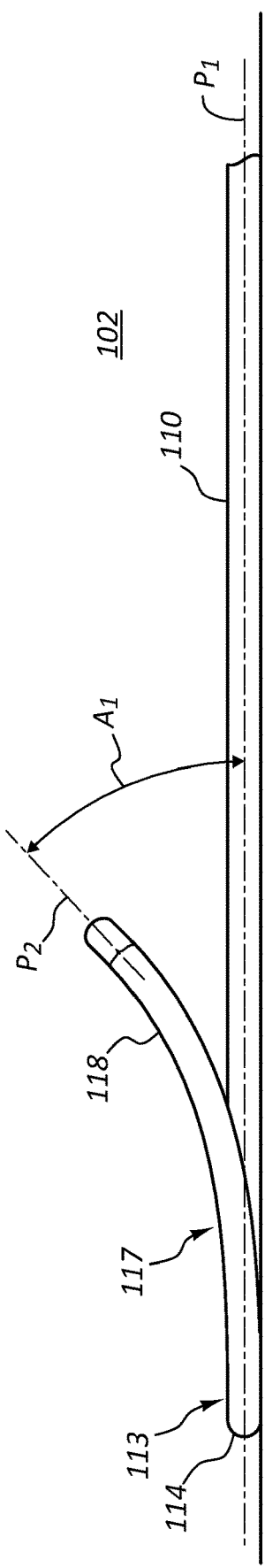

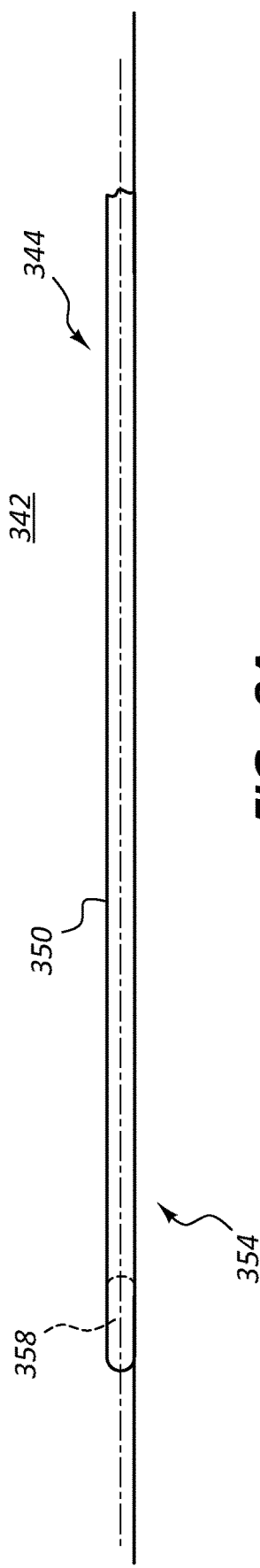
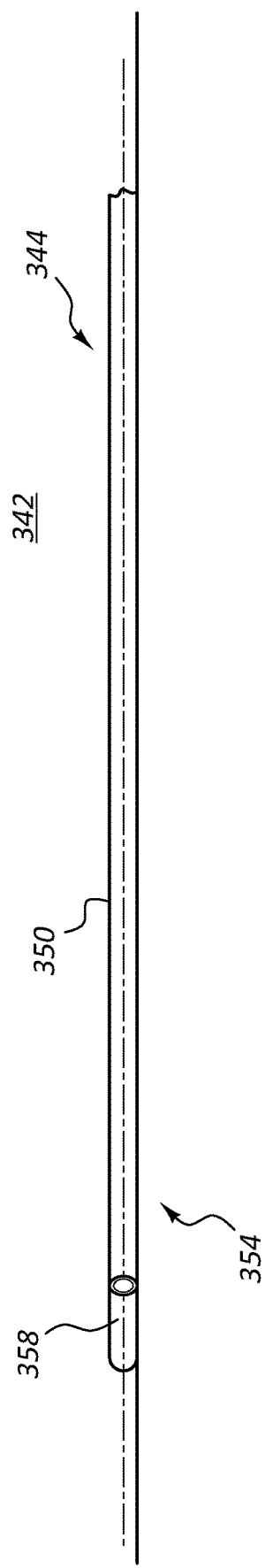

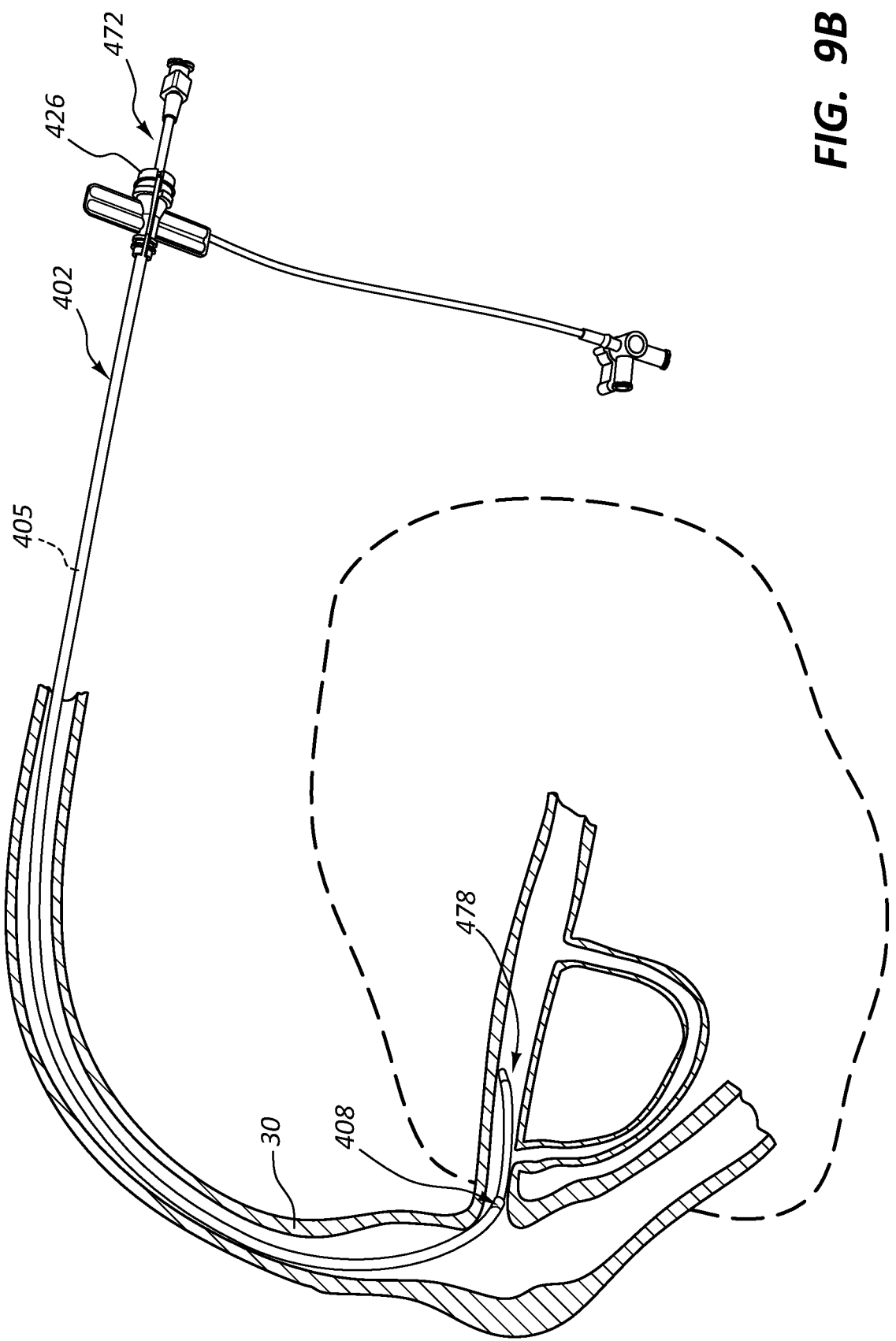

CORONARY ACCESS AND DELIVERY SYSTEMS

RELATED APPLICATIONS

The present application claims priority to U.S. Provisional Application No. 62/309,209, filed on Mar. 16, 2016 and titled "Coronary Access and Delivery Systems" which is hereby incorporated by reference in its entirety.

TECHNICAL FIELD

The present disclosure relates generally to coronary access and delivery systems. More specifically, the present disclosure relates to coronary access guides and introducers. This disclosure also relates to torqueable cores for use with coronary access guides and introducers. Related methods are also disclosed.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 1B is a bottom perspective view of the coronary sinus access system of FIG. 1A.

FIG. 1C is a cross-sectional view of a portion of the coronary sinus guide of FIG. 1B taken through plane 1C-1C.

FIG. 1D is a cross-sectional view of another embodiment of a coronary sinus guide analogous to the coronary sinus guide of FIGS. 1A-1C.

FIG. 3A is a first side view of the portion of the coronary sinus guide of FIG. 2.

FIG. 3B is a second side view of the portion of the coronary sinus guide of FIG. 2.

FIG. 8A is a first side view of a portion of the lateral vein introducer of FIG. 7.

FIG. 8B is a second side view of the portion of the lateral vein introducer of FIG. 7.

FIG. 9B depicts use of a first core to aid in guiding the coronary sinus guide of FIG. 9B.

DETAILED DESCRIPTION

Figure 1A:
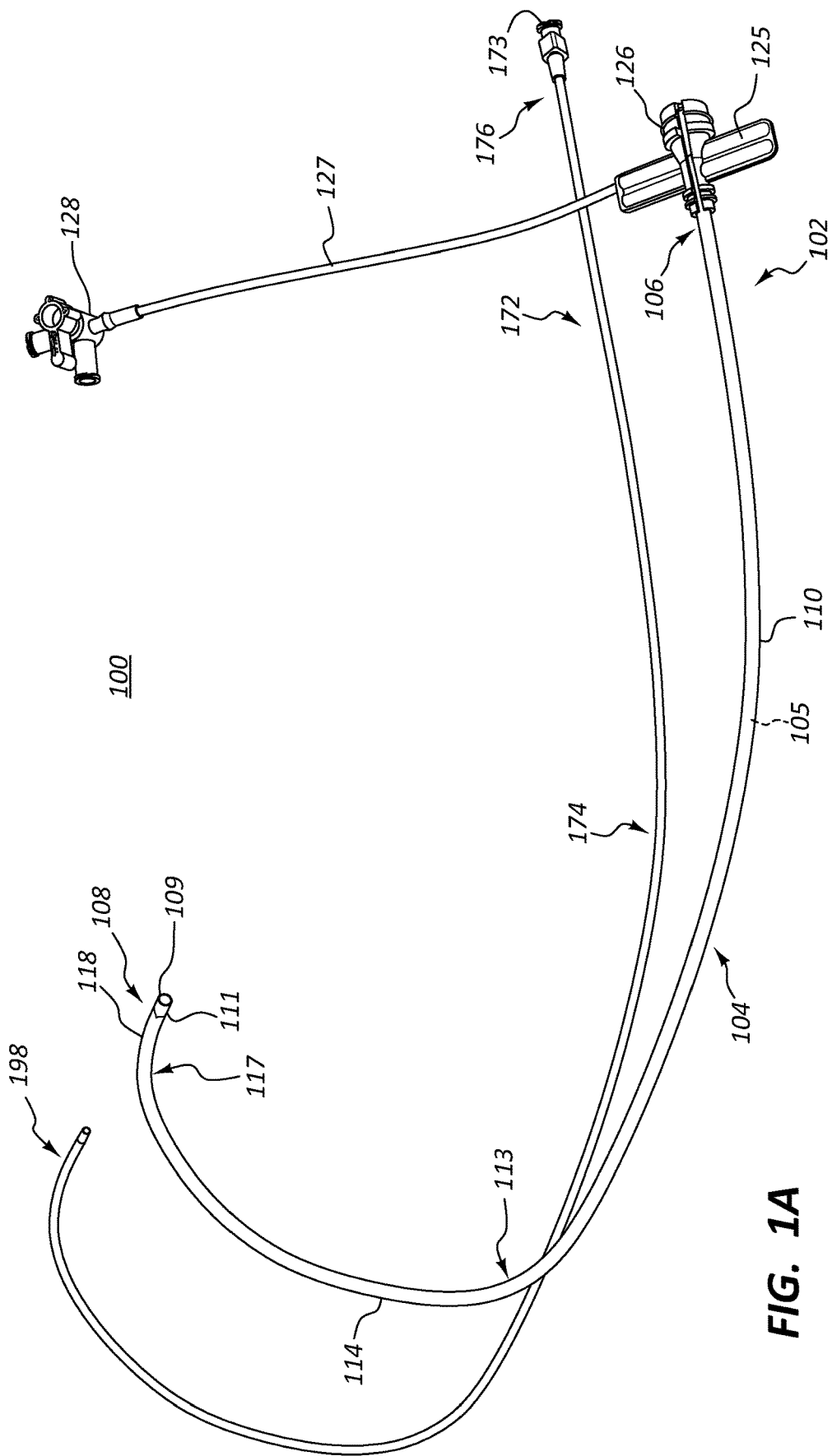
FIG. 1A is a top perspective view of a coronary sinus access system including a coronary sinus guide and a first core.

The various embodiments disclosed herein generally relate to coronary access and delivery systems. In some embodiments, a coronary access system includes a coronary sinus guide and a first core. In certain embodiments, a lateral vein delivery system includes a lateral vein introducer and a second core. The coronary sinus guide, the lateral vein introducer, and the first and second cores may be designed or shaped to access a predetermined position within a heart of a subject. For example, the coronary sinus guide, the lateral vein introducer, and/or the first and second cores can be used in combination to access the predetermined position.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is the portion at the opposite end. For example, the proximal end of a coronary sinus guide is defined as the end closest to the practitioner during utilization of the coronary sinus guide. The distal end is the end opposite the proximal end, along the longitudinal direction of the coronary sinus guide.

The term "pushability" refers to the ability of a component or a device to transfer longitudinal force or longitudinal displacement without being deformed. The term "torqueability" refers to the ability of a component or a device to transfer rotational force or rotational displacement without being deformed.

Some medical procedures can involve the introduction of one or more medical devices into the heart of a subject (e.g., a human patient). For example, electrical leads (e.g., pacemaker leads), defibrillation leads or leads used for cardioversion, specialized catheters (e.g., ablation catheters or sensing catheters), or guidewires may be disposed at one or more positions within the heart to perform cardiac procedures. Some of these medical devices may be flexible and/or pliable. Such flexibility may aid in preventing damage (i.e., to the subject's vasculature) during the use or disposition of such a medical device in a subject. However, due at least in part to such flexibility, it may be difficult to advance such medical devices through a subject's vasculature into the heart without the aid of another medical device that is configured to support or stiffen the flexible medical device. For example, one method of supporting a flexible medical device is to dispose the flexible medical device into or through a lumen of a medical guide or introducer.

In some embodiments, a coronary sinus guide may be configured to aid in the disposition or placement of a medical device (e.g., a small, flexible medical device, such as an electrode lead for use with a pacemaker or defibrillator, and/or for cardioversion) into a coronary sinus of a subject. For example, a coronary sinus guide of the present disclosure may assist a practitioner in the introduction of a pacemaker lead or a defibrillator lead into the coronary sinus of a human heart. Introduction of a medical device into the ostium of the coronary sinus may be difficult as a result of the structure of the heart, the difficulty in locating the coronary sinus using conventional medical technology, and/or the constantly changing shape of the heart while beating as well as the altered anatomy of a heart having cardiomyopathy.

Two approaches are generally used for placement of a medical device within the coronary sinus, an inferior approach from below the heart, and a superior approach from above the heart. In the superior approach, the medical device may be advanced through either the left cephalic or left subclavian vein through the superior vena cava into the right atrium until the medical device is directed toward the coronary sinus. In the inferior approach, the medical device is generally advanced through the femoral vein through the inferior vena cava into the right atrium. The tip of the device is then directed toward the ostium of the coronary sinus. Some embodiments of the coronary access systems, lateral vein delivery systems, and the components thereof, as disclosed herein, may be configured or designed for the superior approach to the coronary sinus. Furthermore, certain embodiments of the coronary access systems, lateral vein delivery systems, and the components thereof may be used or adapted for the inferior approach to the coronary sinus.

The coronary access systems, lateral vein delivery systems, and/or the components thereof of the present disclosure can be used in diseased hearts or in hearts having cardiomyopathy (i.e., hearts that have been enlarged due to cardiomyopathy). Heart anatomy can be altered or changed in hearts having cardiomyopathy. Accordingly, coronary sinus guides, lateral vein introducers, and/or cores having shapes and/or sizes that have been designed for normal hearts or hearts having diseases other than cardiomyopathy may be difficult to use in cardiomyopathic hearts.

FIG. 1A is a top perspective view of a coronary sinus access system 100 including a coronary sinus guide or introducer 102 and a first core 172. FIG. 1B is a bottom perspective view of the coronary sinus access system 100. In some embodiments, an elongate member 104 of the coronary sinus guide 102 has a first shape and an elongate member 174 of the first core 172 has a second shape. As shown, the first shape and the second shape can be similar. Stated another way, the shapes of the elongate members 104, 174 may be complementary. In some other embodiments, the first shape and the second shape may be different in one or more respects.

The coronary sinus guide 102, as depicted, may include a handle 125 that is disposed at and/or coupled to a proximal end 106 of the elongate member 104. The handle 125 may be further coupled to a hub 126. In some embodiments, a sidearm catheter 127 may be coupled to and/or in fluid communication with the hub 126. Additionally, the sidearm catheter 127 may also be coupled to a hemostatic valve 128. As depicted, a hub 173 may be coupled to a proximal end 176 of the first core 172.

As illustrated, the elongate member 104 includes the proximal end 106 and a distal end 108. In some embodiments, the elongate member 104 may include a lumen 105 extending between each of the proximal end 106 and the distal end 108 of the elongate member 104. For example, the elongate member 104 may have an inside diameter of 9 French. In various embodiments, the inside diameter may be between about 4 French and about 16 French, between about 6 French and about 12 French, between about 8 French and about 10 French, or another suitable inside diameter. Accordingly, the lumen 105 of the elongate member 104 may be configured to receive the first core 172, wherein an outside diameter of the first core 172 may be between about 4 French and about 16 French, between about 6 French and about 12 French, between about 8 French and about 10 French, or another suitable diameter.

In some other embodiments, the elongate member 104 may include a lumen extending through only a portion of the length of the elongate member 104. In yet some other embodiments, the elongate member 104 may lack a lumen (i.e., the elongate member may be solid). In some embodiments, the elongate member 104 may include more than one lumen. For example, the elongate member 104 may include two, three, four, or more lumens.

In various embodiments, the elongate member 104 may include a proximal portion 110 extending distally from the proximal end 106 of the elongate member 104. The proximal portion 110 may be curved. Specifically, as depicted, the proximal portion 110 may be slightly curved or have a low curvature. In certain embodiments, only a portion of the proximal portion 110 may be curved. In certain other embodiments, the proximal portion 110 may be substantially linear or straight. The elongate member 104 may also include a medial portion 114 extending distally from the proximal portion 110. As shown, the medial portion 114 may be curved, for example, the medial portion 114 may curve through a substantially circular arc. In certain embodiments, only a portion of the medial portion 114 may be curved. In certain other embodiments, the medial portion 114 may be substantially linear or straight.

The elongate member 104 may further include a distal portion 118 extending distally from the medial portion 114, and, as illustrated, the distal portion 118 may terminate at a distal tip 109. The distal tip 109 may be formed from a more flexible, pliable, and/or compressible material than the remaining portions or components of the coronary sinus guide 102 (i.e., the distal tip 109 may be atraumatic). Such a configuration of the distal tip 109 may aid in limiting or preventing damage to the vasculature of a subject, for example, when the coronary sinus guide 102 is in use in the subject. Furthermore, a marker 111, such as a radiopaque band, may be disposed at or adjacent the distal tip 109 to aid in placement or use of the coronary sinus guide 102 (i.e., during a medical procedure). In some other embodiments, the coronary sinus guide 102 may include two, three, or more markers such as marker 111. One or more such markers may also be disposed at other positions along the coronary sinus guide 102 (e.g., at or adjacent the medial portion 114).

As depicted, the distal portion 118 may be substantially linear or straight. In certain embodiments, the distal portion 118 may be curved, for example, the distal portion 118 may curve through a substantially circular arc. In certain other embodiments, only a portion of the distal portion 118 may be curved.

With continued reference to FIGS. 1A and 1B, a first transition portion 113 may be disposed or extend between each of the proximal portion 110 and the medial portion 114. Similarly, a second transition portion 117 may be disposed or extend between each of the medial portion 114 and the distal portion 118. In some embodiments, the first transition portion 113 and/or the second transition portion 117 may be curved, for example, the first transition portion 113 and/or the second transition portion 117 may curve through substantially circular arcs. The first transition portion 113 and/or the second transition portion 117 may also provide substantially smooth transitions between portions of the elongate member 104. For example, the first transition portion 113 may provide a substantially smooth transition between the shape of the proximal portion 110 and the shape of the medial portion 114 such that the slight curve of the proximal portion 110 may smoothly continue into the curve of the medial portion 114. Analogously, the second transition portion 117 may provide a substantially smooth transition between the shape of the medial portion 114 and the shape of the distal portion 118.

In some embodiments, the proximal portion 110, the medial portion 114, the distal portion 118, and/or other components of the elongate member 104 may be integrally formed. In some other embodiments, the proximal portion 110, the medial portion 114, the distal portion 118, and/or other components of the elongate member 104 may be discretely or separately formed. The elongate member 104 can be flexible or pliable. While being flexible, however, the elongate member 104 can also be formed to have a shape memory. For example, the coronary sinus guide 102 may be formed from a material having a shape memory and/or from a material that permits distortion from and substantial return to a desired or predetermined shape (e.g., polyethylene, polyurethane, etc.). When the elongate member 104 is in an unconstrained configuration (i.e., when the elongate member 104 is not disposed within a subject's vasculature and/or is disposed on a flat surface), the elongate member 104 may generally assume a shape as depicted, for example, in FIGS. 1A and 1B. On the other hand, the shape of the elongate member 104 may not be so rigid that the elongate member 104 will not conform to the vasculature of a subject. Such flexibility can limit or reduce a risk of injury or trauma to the subject. Additionally, the coronary sinus guide 102, or portions thereof, may be formed from a biocompatible material. For example, the coronary sinus guide 102 may be formed from a material that is suitable for use in humans.

Figure 2:
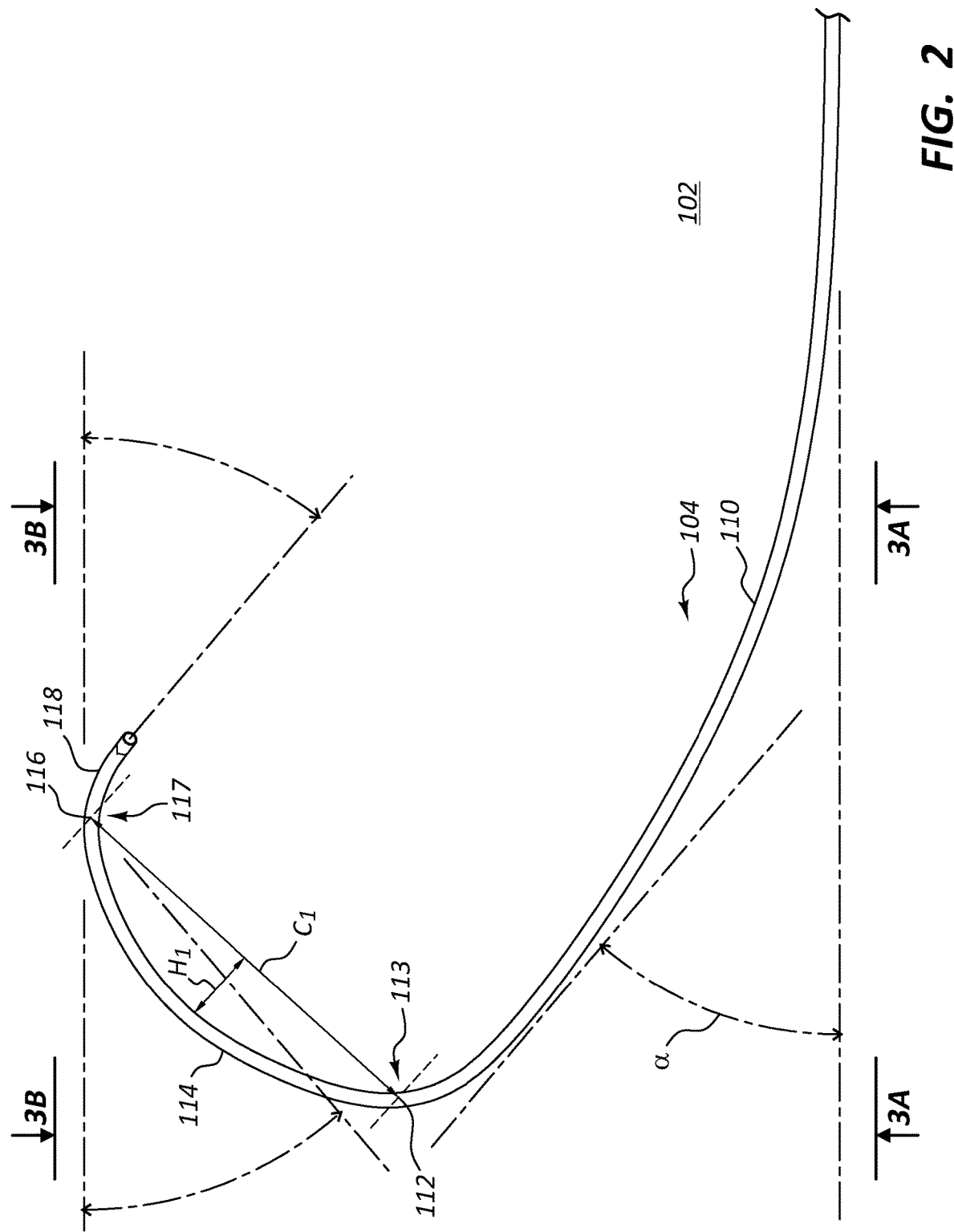
FIG. 2 is a top view of a portion of the coronary sinus guide of FIGS. 1A and 1B.

FIG. 2 is a top view of a portion of the coronary sinus guide 102 of FIGS. 1A and 1B. As discussed above, the medial portion 114 can curve through a substantially circular arc. The substantially circular arc of the medial portion 114 may be defined by a chord $C_1$ of predetermined length, wherein the chord $C_1$ extends between the longitudinal axis of the elongate member 104 at a junction 112 of the proximal portion 110 and the medial portion 114 and the longitudinal axis of the elongate member 104 at a junction 116 of the medial portion 114 and the distal portion 118. In certain embodiments, the junction 112 may be disposed at a position at a midpoint of the first transition portion 113. Similarly, the junction 116 may be disposed at a position at a midpoint of the second transition portion 117. Furthermore, the medial portion 114 may have a predetermined height $H_1$ above the chord $C_1$.

In some embodiments, the length of the chord $C_1$ may be between about 5 cm and about 25 cm, between about 10 cm and about 20 cm, between about 12 cm and about 18 cm, between about 14 cm and about 16 cm, or another suitable length. In certain embodiments, the height $H_1$ of the medial portion 114 above the chord $C_1$ may be between about 1 cm and about 9 cm, between about 2 cm and about 8 cm, between about 4 cm and about 6 cm, or another suitable height.

In various embodiments, the length of the proximal portion 110 (i.e., along the longitudinal axis of the proximal portion 110) may be greater than a length of the medial portion 114. Furthermore, the length of the medial portion 114 (i.e., along the longitudinal axis of the medial portion 114) may be greater than the length of the distal portion 118 (i.e., along the longitudinal axis of the distal portion 118). In various other embodiments, the length of the proximal portion 110 may be less than or substantially equal to the length of the medial portion 114. Likewise, the length of the medial portion 114 may be less than or substantially equal to the length of the distal portion 118. Other combinations of the lengths of the proximal portion 110, the medial portion 114, and/or the distal portion 118 are also within the scope of this disclosure.

In certain embodiments, the length of the proximal portion 110 may be at least about 15 cm. In certain other embodiments, the length of the proximal portion 110 may be between about 10 cm and about 50 cm, between about 20 cm and about 40 cm, between about 25 cm and about 35 cm, or another suitable length. The length of the medial portion 114 may be between about 5 cm and about 35 cm, between about 10 cm and about 30 cm, between about 15 cm and about 25 cm, or another suitable length. Furthermore, the length of the distal portion 118 may be between about 0.5 cm and about 10 cm, between about 1 cm and about 8 cm, between about 2 cm and about 6 cm, or another suitable length.

In various embodiments, the radii of curvature of the each of the first transition portion 113, the medial portion 114, and the second transition portion 117 may be different. In various other embodiments, the radii of curvature of the each of the first transition portion 113, the medial portion 114, and the second transition portion 117 may be substantially equal. Other combinations of radii of curvature of the first transition portion 113, the medial portion 114, and the second transition portion 117 are also within the scope of this disclosure. For example, the radii of curvature of the first transition portion 113 and the second transition portion 117 may be substantially equal, while the radius of curvature of the medial portion 114 may be different than the radii of curvature of the first transition portion 113 and the second transition portion 117.

In some embodiments, the magnitude of the angle α may be between about 0° and about 90°, between about 25° and about 65°, between about 40° and about 50°, or another suitable magnitude.

Furthermore, the elongate member 104, the handle 125, and/or the hub 126 may be longitudinally openable and/or separable. Stated another way, the elongate member 104, the handle 125, and/or the hub 126 may be splittable, sliceable, and/or tearable to allow or permit the coronary sinus guide 102 to be separated into two lengthwise portions, for example, as the coronary sinus guide 102 is removed from the subject. Once the coronary sinus guide 102 has been separated, the coronary sinus guide 102 can be removed from the operating theater. In some embodiments, a proximal end of a lead may be coupled to a connector or may be directly coupled to a pulse generator of a pacemaker, as such, it may be desirable that the coronary sinus guide 102 is separable to allow or permit it to be separated into two lengthwise portions as it is removed from the subject's body. In some other embodiments, the coronary sinus guide 102 may not be longitudinally openable or separable. For example, if a lead is relatively small and/or is not connected to a pulse generator and the lumen 105 of the elongate member 104 is relatively large, the coronary sinus guide 102 may not need to be longitudinally openable or separable.

FIG. 1C is a cross-sectional view of a portion of the coronary sinus guide 102 taken through plane 1C-1C of FIG. 1B. The lumen 105 is shown within the elongate member 104.

The stiffness of the coronary sinus guide 102 may be enhanced by disposing one or more reinforcement members along a portion of the coronary sinus guide 102. In some embodiments, a reinforcement member may be disposed within, and extend longitudinally along, the elongate member 104 of the coronary sinus guide 102. For example, FIG. 1D is a cross-sectional view of a portion of another embodiment of a coronary sinus guide 102', analogous to the coronary sinus guide 102 of FIGS. 1A-1C. The coronary sinus guide 102' of FIG. 1D differs from the coronary sinus guide 102 of FIGS. 1A-1C only with respect to the addition of two reinforcement members 101' extending along the elongate member 104'. These reinforcement members 101' may extend along any portion of the length of the elongate member 104'. In some instances the reinforcement members 101' may facilitate the transfer of longitudinal force along the coronary sinus guide 102'. In other words, the reinforcement members 101' may enhance pushability of the coronary sinus guide 102' in some embodiments.

The reinforcement members 101' may comprise metal wires, polymer strands, braided strands, and so forth. In some embodiments the reinforcement members comprise nitinol wires. Reinforcement members 101' extending longitudinally along the coronary sinus guide 102' may reinforce the coronary sinus guide 102' longitudinally, while still allowing the coronary sinus guide 102' to be longitudinally split by a user. Coronary sinus guides comprising one, two, three, four, five, or any other number of reinforcement members 101' are within the scope of this disclosure. In the embodiment of FIG. 1D, the reinforcement members 101' are disposed at 180° to each other, embodiments wherein any number of reinforcement members 101' are evenly spaced around the circumference of the elongate member 104', as well as embodiments wherein the reinforcement members 101' are disposed in some other pattern, are within the scope of this disclosure.

FIG. 3A is a first side view of a portion of the coronary sinus guide 102 of FIG. 2. FIG. 3B is a second side view of the portion of the coronary sinus guide 102 of FIG. 2, which is opposite of the first side view. Various components of the coronary sinus guide 102 can be disposed in different planes (i.e., two, three, or more planes) when the coronary sinus guide 102 is disposed in the unconstrained configuration. As depicted, the proximal portion 110, the first transition portion 113, the medial portion 114, and/or at least a portion of the second transition portion 117 can be disposed in a first plane $P_1$. Furthermore, the distal portion 118 and/or at least a portion of the second transition portion 117 can be disposed in a second plane $P_2$. The second transition portion 117 and/or other components of the coronary sinus guide 102 can also curve or transition (i.e., stepwise) between each of the first plane $P_1$ and the second plane $P_2$. The coronary sinus guide 102 can be flexible, however, and upon disposition of a portion of the coronary sinus guide 102 within a vasculature of a subject, one or more portions of the coronary sinus guide 102 may conform to the three-dimensional shape of the vasculature.

As illustrated, a dihedral angle $A_1$ can be disposed between the first plane $P_1$ and the second plane $P_2$. In some embodiments, the magnitude of the dihedral angle $A_1$ may be between about 5° and about 35°, between about 10° and about 30°, between about 15° and about 25°, or another suitable magnitude.

In some embodiments, the first core 172 may be torqueable, meaning that the proximal end 176 of the first core 172 can be rotated by a practitioner and a distal end 198 of the first core 172 will rotate by a corresponding amount (see, e.g., FIGS. 1A and 1B). Stated another way, while the first core 172 may be laterally flexible the first core 172 may also be torsionally stiff. In contrast, the coronary sinus guide 102 may be both laterally and torsionally flexible.

The stiffness of the first core 172 may be enhanced by: increasing the thickness of the material forming the first core 172; forming the first core 172 from a stiff material; and/or disposing a reinforcement member such as a braid (e.g., a metal or fibrous braid) or one or more wires (e.g., nitinol wires) within a portion of the first core 172. The reinforcement member may enhance pushability and/or torqueability of the first core 172. In some embodiments, a braided reinforcement and/or a wire reinforcement may run along a length of the first core 172, such that the first core 172 is torsionally stiff while being radially flexible.

The first core 172 may be disposable within or configured to be disposed within the lumen 105 of the coronary sinus guide 102. Such a coupling of the first core 172 and the coronary sinus guide 102 may render the combination of the first core 172 and the coronary sinus guide 102 torqueable (wherein the coronary sinus guide 102 alone is not substantially torqueable). In some embodiments, the first core 172 and the coronary sinus guide 102 may be coupled by: frictional engagement between an outer surface of the first core 172 and an inner surface of the lumen 105 of the coronary sinus guide 102; coupling together of a hub of the coronary sinus guide 102 with a hub of the first core 172; and/or an interference fit between the first core 172 and a similarly shaped coronary sinus guide 102. For example, upon disposition of the first core 172 within the lumen 105 of the coronary sinus guide 102, a frictional coupling or binding may occur between the inner surface of the lumen 105 of the coronary sinus guide 102 and the outer surface of the first core 172. Such a coupling may permit or allow the distal end 108 of the coronary sinus guide 102 to be rotated when a proximal end 176 of the first core 172 is rotated.

Figure 4:
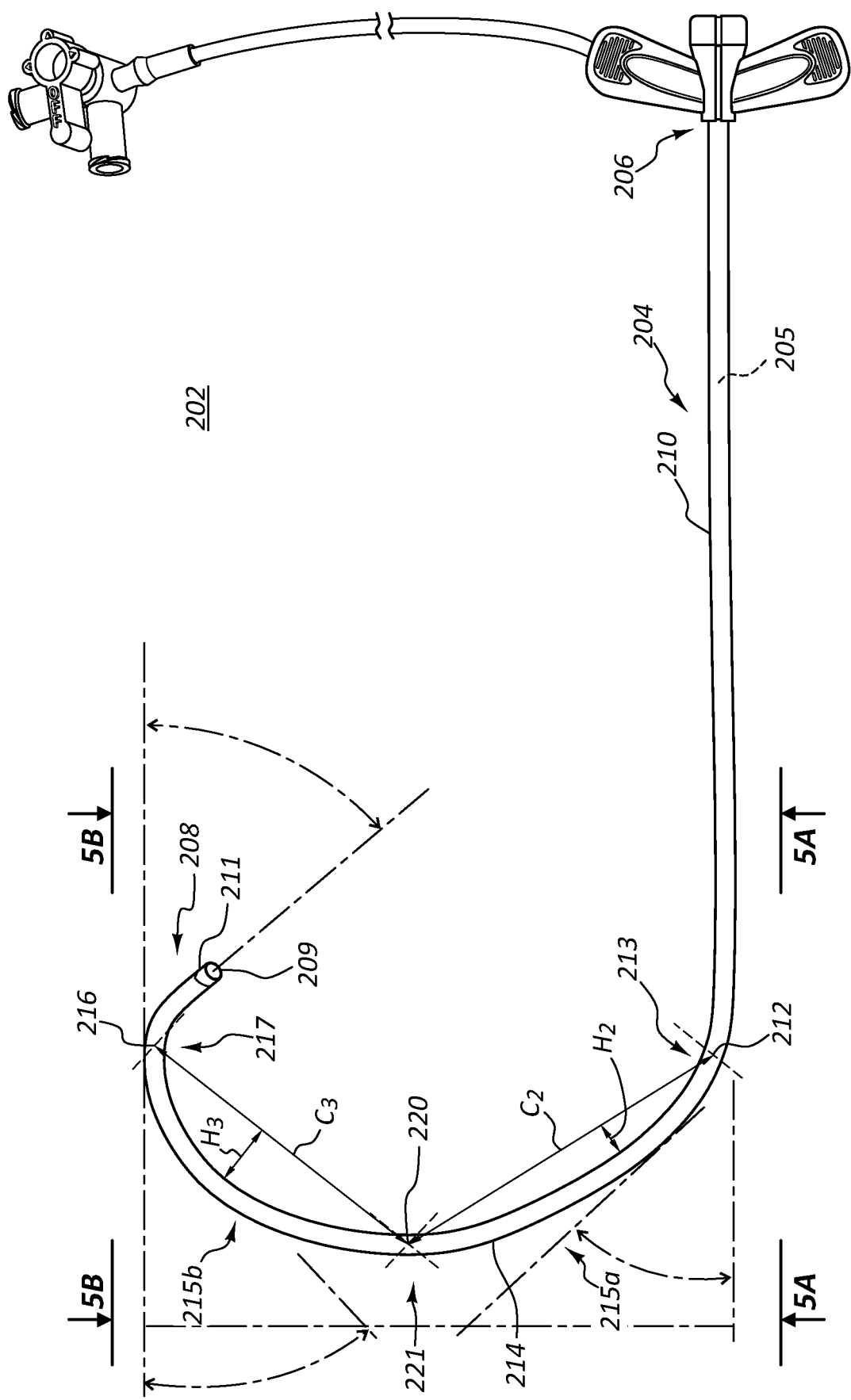
FIG. 4 is a top view of another embodiment of a coronary sinus guide.

FIG. 4 is a top view of another embodiment of a coronary sinus guide 202 that can, in certain respects, resemble components of the coronary sinus guide 102 described in connection with FIGS. 1A-3B. It will be appreciated that all the illustrated embodiments may have analogous features. Accordingly, like features are designated with like reference numerals, with the leading digits incremented to "2." For instance, the elongate member is designated as "104" in FIGS. 1A-3B, and an analogous elongate member is designated as "204" in FIG. 4. Relevant disclosure set forth above regarding similarly identified features thus may not be repeated hereafter. Moreover, specific features of the coronary sinus access system 100 and related components shown in FIGS. 1A-3B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the coronary sinus access system of FIG. 4. Any suitable combination of the features, and variations of the same, described with respect to the coronary sinus access system 100 and components illustrated in FIGS. 1A-3B can be employed with the coronary sinus access system and components of FIG. 4, and vice versa. This pattern of disclosure applies equally to further embodiments depicted in subsequent figures and described hereafter.

As shown in FIG. 4, the coronary sinus guide 202 can include an elongate member 204 having a proximal end 206 and a distal end 208. In some embodiments, the elongate member 204 may include a lumen 205 extending between each of the proximal end 206 and the distal end 208 of the elongate member 204. The elongate member 204 may have an inside diameter of 9 French. In various embodiments, the inside diameter may be between about 4 French and about 16 French, between about 6 French and about 12 French, between about 8 French and about 10 French, or another suitable diameter. Accordingly, the lumen 205 of the elongate member 204 may be configured to receive a core, analogous to the first core 172, wherein an outside diameter of the core may be between about 4 French and about 16 French, between about 6 French and about 12 French, between about 8 French and about 10 French, or another suitable diameter.

In some other embodiments, the elongate member 204 may include a lumen extending through only a portion of the length of the elongate member 204. In yet some other embodiments, the elongate member 204 may lack a lumen. In some embodiments, the elongate member 204 may include more than one lumen. For example, the elongate member 204 may include two, three, four, or more lumens.

In various embodiments, the elongate member 204 may include a proximal portion 210 extending distally from the proximal end 206 of the elongate member 204. As depicted, the proximal portion 210 may be substantially linear or straight. In certain embodiments, a portion of the proximal portion 210 may be curved.

As illustrated, the elongate member 204 can also include a medial portion 214 extending distally from the proximal portion 210. As shown, the medial portion 214 can be curved. Furthermore, the medial portion 214 may include a first subportion or proximal subportion 215a and a second subportion or distal subportion 215b. For example, the first subportion 215a may curve through a substantially circular arc having a first magnitude and the second subportion 215b may curve through a substantially circular arc having a second magnitude. In certain embodiments, only one of the first or second subportions 215a, 215b of the medial portion 214 may be curved.

With continued reference to FIG. 4, a first transition portion 213 may be disposed or extend between each of the proximal portion 210 and the medial portion 214. A second transition portion 217 may be disposed or extend between each of the medial portion 214 and a distal portion 218. Similarly, a third transition portion 221 may be disposed or extend between each of the first subportion 215a and the second subportion 215b. In some embodiments, the first transition portion 213, the second transition portion 217, and/or the third transition portion 221 may be curved. For example, the first transition portion 213, the second transition portion 217, and/or the third transition portion 221 may curve through substantially circular arcs. Additionally, the first transition portion 213, the second transition portion 217, and/or the third transition portion 221 may provide substantially smooth transitions between portions and/or subportions of the elongate member 204.

In some embodiments, the radii of curvature of the each of the first transition portion 213, the second transition portion 217, the third transition portion 221, the medial portion 214, the first subportion 215a, and the second subportion 215b may be different. In various other embodiments, the radii of curvature of the each of the first transition portion 213, the second transition portion 217, the third transition portion 221, the medial portion 214, the first subportion 215a, and the second subportion 215b may be substantially equal. Other combinations of radii of curvature of the first transition portion 213, the second transition portion 217, the third transition portion 221, the medial portion 214, the first subportion 215a, and the second subportion 215b are also within the scope of this disclosure. For example, the radii of curvature of the first transition portion 213, the second transition portion 217, and the third transition portion 221 may be substantially equal, while the radii of curvature of the first subportion 215a and the second subportion 215b may be different than the radii of curvature of the first transition portion 213, the second transition portion 217, and the third transition portion 221.

The substantially circular arc of the first subportion 215a may be defined by a chord $C_2$ of predetermined length, wherein the chord $C_2$ extends between the longitudinal axis of the elongate member 204 at a junction 212 of the proximal portion 210 and the medial portion 214 and the longitudinal axis of the elongate member 204 at a junction 220 of the first subportion 215a and the second subportion 215b. In certain embodiments, the junction 212 may be a position at a midpoint of the first transition portion 213. Similarly, the junction 220 may be a position at a midpoint of the third transition portion 221. Furthermore, the first subportion 215a may have a predetermined height $H_2$ above the chord $C_2$. Analogously, the substantially circular arc of the second subportion 215b may be defined by a chord $C_3$ of predetermined length, wherein the chord $C_3$ extends between the longitudinal axis of the elongate member 204 at the junction 220 and the longitudinal axis of the elongate member 204 at a junction 216 of the second subportion 215b and the distal portion 218. In certain embodiments, the junction 216 may be a position at a midpoint of the second transition portion 217. The second subportion 215b may have a predetermined height $H_3$ above the chord $C_3$. Furthermore, in various embodiments, a distance $D_2$ between the junction 116 and the junction 220 may be between about 4 cm and about 22 cm, between about 8 cm and about 18 cm, between about 12 cm and about 14 cm, or another suitable distance.

In some embodiments, the length of the chord $C_2$ may be between about 2 cm and about 16 cm, between about 4 cm and about 14 cm, between about 6 cm and about 12 cm, between about 8 cm and about 10 cm, or another suitable length. In certain embodiments, the height $H_2$ of the first subportion 215a above the chord $C_2$ may be between about 0.5 cm and about 7 cm, between about 1 cm and about 5 cm, between about 1.5 cm and about 3 cm, or another suitable height. In various embodiments, the length of the chord $C_3$ may be between about 2 cm and about 14 cm, between about 3 cm and about 10 cm, between about 4 cm and about 8 cm, between about 5 cm and about 7 cm, or another suitable length. In certain embodiments, the height $H_3$ of the second subportion 215b above the chord $C_3$ may be between about 0.25 cm and about 6 cm, between about 0.5 cm and about 4 cm, between about 1 cm and about 3 cm, or another suitable height.

The elongate member 204 may further include the distal portion 218 extending distally from the medial portion 214, and, as illustrated, the distal portion 218 may terminate at a distal tip 209. As discussed above, the distal tip 209 may be formed from a more flexible, pliable, and/or compressible material than the remaining portions or components of the coronary sinus guide 202. Furthermore, a marker 211 such as a radiopaque band may be disposed at or adjacent the distal tip 209 or at another suitable location.

As depicted, the distal portion 218 may be substantially linear or straight. In certain embodiments, the distal portion 218 may be curved, for example, the distal portion 218 may curve through a substantially circular arc. In certain other embodiments, only a portion of the distal portion 218 may be curved.

In various embodiments, the length of the proximal portion 210 (i.e., along the longitudinal axis of the proximal portion 210) may be greater than the length of the medial portion 214 (i.e., along the longitudinal axis of the medial portion 214). Furthermore, the length of the medial portion 214 may be greater than the length of the distal portion 218 (i.e., along the longitudinal axis of the distal portion 218). In various other embodiments, the length of the proximal portion 210 may be less than or substantially equal to the length of the medial portion 214. Likewise, the length of the medial portion 214 may be less than or substantially equal to the length of the distal portion 218. The length of the first subportion 215a (i.e., along the longitudinal axis of the first subportion 215a) may be substantially equal to the length of the second subportion 215b (i.e., along the longitudinal axis of the first subportion 215a). In some embodiments, the length of the first subportion 215a may be greater than the length of the second subportion 215b, or vice versa. Other combinations of the lengths of the proximal portion 210, the medial portion 214, the first subportion 215a, the second subportion 215b, and/or the distal portion 218 are also within the scope of this disclosure.

In certain embodiments, the length of the proximal portion 210 may be at least about 15 cm. In certain other embodiments, the length of the proximal portion 210 may be between about 10 cm and about 40 cm, between about 14 cm and about 30 cm, between about 18 cm and about 25 cm, or another suitable length. The length of the medial portion 214 may be between about 5 cm and about 30 cm, between about 10 cm and about 25 cm, between about 15 cm and about 20 cm, or another suitable length. The length of the first subportion 215a may be between about 3 cm and about 16 cm, between about 5 cm and about 13 cm, between about 7 cm and about 9 cm, or another suitable length. The length of the second subportion 215b may be between about 2 cm and about 14 cm, between about 4 cm and about 12 cm, between about 5 cm and about 8 cm, or another suitable length. Furthermore, the length of the distal portion 218 may be between about 0.5 cm and about 10 cm, between about 1 cm and about 8 cm, between about 2 cm and about 6 cm, or another suitable length.

As discussed above regarding the elongate member 104, the elongate member 204 may be longitudinally openable and/or separable. In some other embodiments, the elongate member 204 may not be longitudinally openable or separable. Furthermore, in some embodiments the coronary sinus guide 202 may comprise reinforcement members analogous to the reinforcement members 101' of FIG. 1C.

Figure 5A:
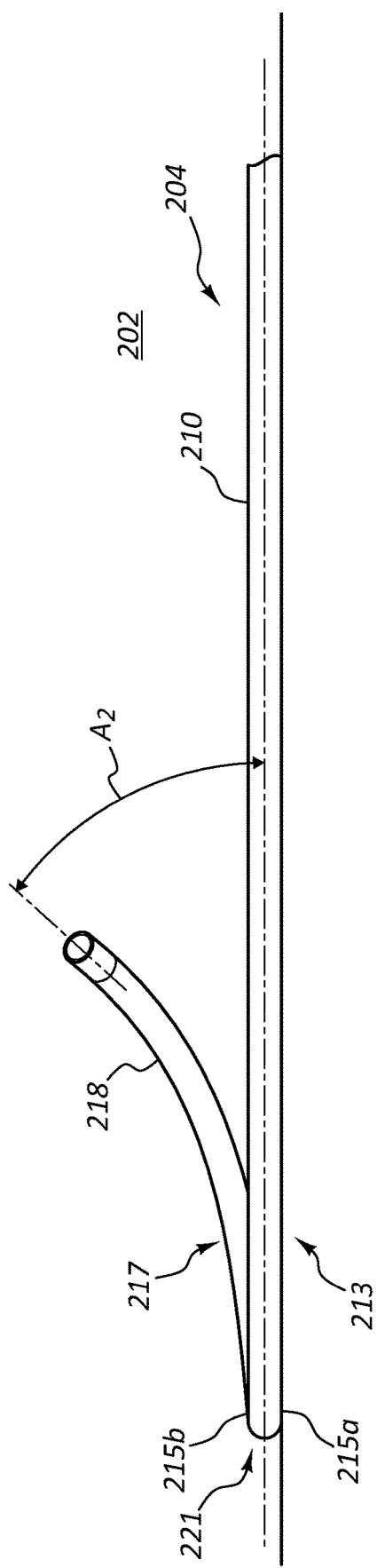
FIG. 5A is a first side view of a portion of the coronary sinus guide of FIG. 4.
Figure 5B:
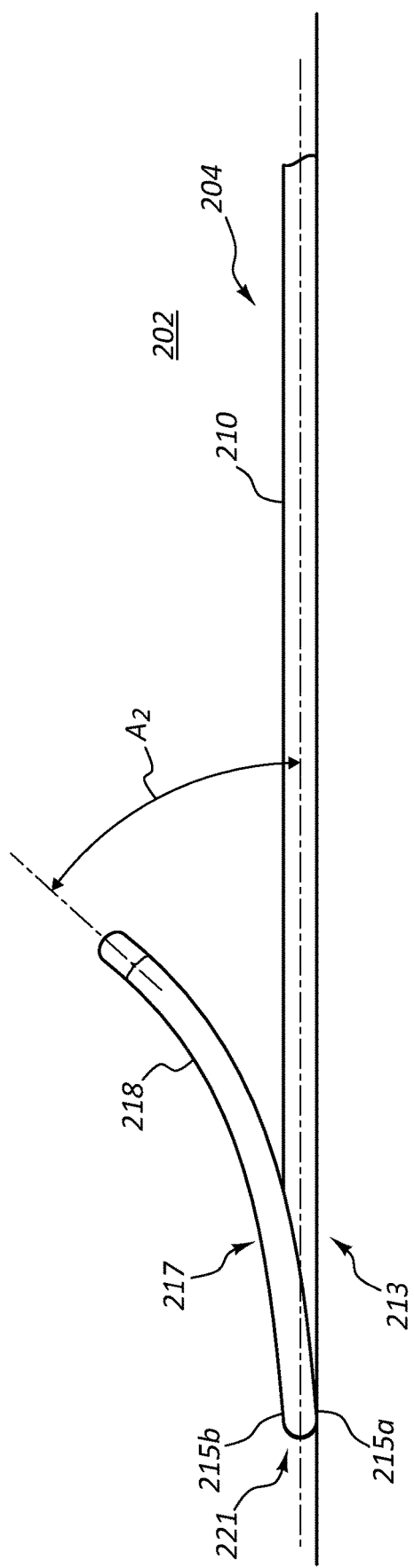
FIG. 5B is a second side view of the portion of the coronary sinus guide of FIG. 4.

FIG. 5A is a first side view of a portion of the coronary sinus guide 202 of FIG. 4. FIG. 5B is a second side view of the portion of the coronary sinus guide 202 of FIG. 4, which is opposite of the first side view. Various components of the coronary sinus guide 202 can be disposed in different planes when the coronary sinus guide 202 is disposed in the unconstrained configuration. As depicted, the proximal portion 210, the first transition portion 213, the first subportion 215a, the third transition portion 221, and at least a portion of the second subportion 215b, and the second transition portion 217 can be disposed in a first plane $P_1$. In some embodiments, a portion of the elongate member 204 (e.g., the second transition portion 217) may curve or transition between the first plane $P_1$ and a second plane $P_2$. Furthermore, the distal portion 218 and at least a portion of the second transition portion 217 can be disposed in the second plane $P_2$. The coronary sinus guide 202 can be flexible, however, and upon disposition of a portion of the coronary sinus guide 202 within a vasculature of a subject, one or more portions of the coronary sinus guide 202 may conform to the three-dimensional shape of the vasculature.

As illustrated, a dihedral angle $A_2$ can be disposed between the first plane $P_1$ and the second plane $P_2$. In some embodiments, the magnitude of the dihedral angle $A_2$ may be between about 30° and about 70°, between about 40° and about 60°, between about 45° and about 55°, or another suitable magnitude.

Figure 6:
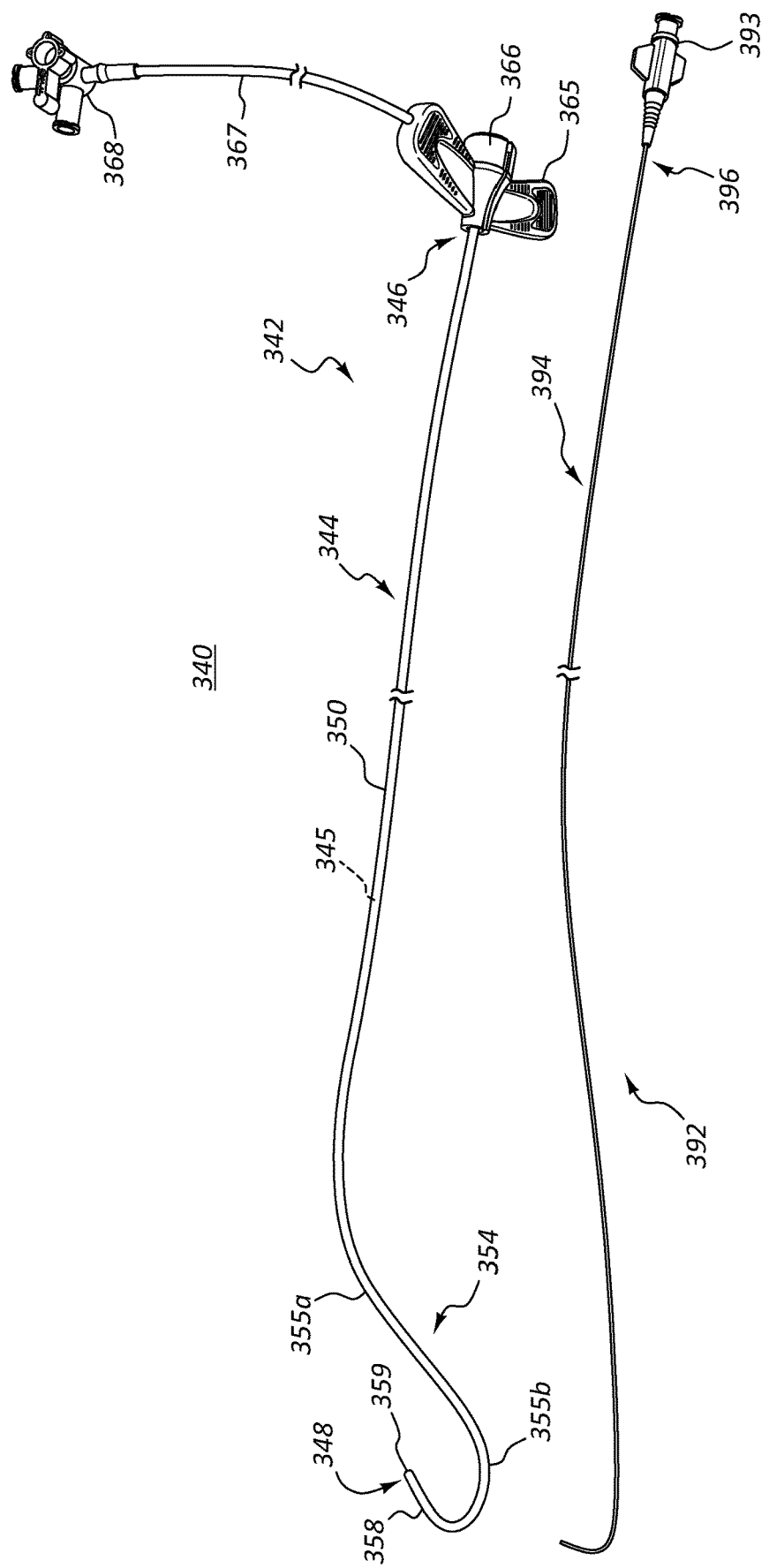
FIG. 6 is a perspective view of a lateral vein delivery system including a lateral vein introducer and a second core.

FIG. 6 is a perspective view of a lateral vein delivery system or vascular delivery system 340 including a lateral vein introducer or outer sheath 342 and a second core 392. In some embodiments, an elongate member 344 of the lateral vein introducer 342 has a first shape and an elongate member 394 of the second core 392 has a second shape. As shown, the first shape and the second shape may be different. In some other embodiments, the first shape and the second shape may be similar. For example, the elongate members 344, 394 may be substantially similarly shaped.

The lateral vein introducer 342, as depicted, may include a handle 365 that is disposed at and/or coupled to a proximal end 346 of the elongate member 344. The handle 365 may be further coupled to a hub 366. In some embodiments, a sidearm catheter 367 may be coupled to and/or in fluid communication with the hub 366. Additionally, the sidearm catheter 367 may also be coupled to a hemostatic valve 368. As depicted, a hub 393 may be coupled to a proximal end 396 of the second core 392.

As illustrated, the elongate member 344 includes the proximal end 346 and a distal end 348. In some embodiments, the elongate member 344 may include a lumen 345 extending between each of the proximal end 346 and the distal end 348 of the elongate member 344. For example, the elongate member 344 may have an inside diameter of 7 French. In various embodiments, the inside diameter may be between about 2 French and about 12 French, between about 4 French and about 10 French, between about 6 French and about 8 French, or another suitable diameter. Accordingly, the lumen 345 of the elongate member 344 may be configured to receive the second core 392, wherein an outside diameter of the second core 392 may be between about 2 French and about 12 French, between about 4 French and about 10 French, between about 6 French and about 8 French, or another suitable diameter.

In some other embodiments, the elongate member 344 may include a lumen extending through only a portion of the length of the elongate member 344. In yet some other embodiments, the elongate member 344 may lack a lumen (i.e., the elongate member may be solid). In some embodiments, the elongate member 344 may include more than one lumen. For example, the elongate member 344 may include two, three, four, or more lumens.

In various embodiments, the elongate member 344 may include a proximal portion 350 extending distally from the proximal end 346 of the elongate member 344. As depicted, the proximal portion 350 may be substantially linear or straight. In certain embodiments, at least a portion of the proximal portion 350 may be curved. The elongate member 344 may also include an S-shaped portion or medial portion 354 extending distally from the proximal portion 350. As shown, the S-shaped portion 354 may be curved, for example, the S-shaped portion 354 may curve through a substantially sigmoid curve. Furthermore, the S-shaped portion 354 may include a first subportion or proximal subportion 355a and a second subportion or distal subportion 355b. For example, the first subportion 355a may curve through a substantially circular arc having a first magnitude (e.g., a first arc) and the second subportion 355b may curve through a substantially circular arc having a second magnitude (e.g., a second arc). In some embodiments, the radius of curvature of the first arc can be greater than the radius of curvature of the second arc, or vice versa. In some other embodiments, the radius of curvature of the first arc may be substantially equal to the radius of curvature of the second arc.

Additionally, the first subportion 355a may curve in a first direction or orientation and the second subportion 355b may curve in a second direction or orientation. For example, the orientation of the first subportion 355a may be substantially opposite of the orientation of the second subportion 355b. In certain embodiments, only one of the first or second subportions 355a, 355b of the S-shaped portion or medial portion 354 may be curved.

The elongate member 344 may further include a distal portion 358 extending distally from the S-shaped portion 354, and, as illustrated, the distal portion 358 may terminate at a distal tip 359. As described above regarding the distal tips 109, 209, the distal tip 359 may be formed from a more flexible, pliable, and/or compressible material than the remaining portions or components of the lateral vein introducer 342 (i.e., the distal tip 359 may be atraumatic). Furthermore, one or more markers, such as a radiopaque band, may be disposed at or adjacent the distal tip 359, or at another suitable position, to aid in placement or use of the lateral vein introducer 342 (i.e., during a medical procedure).

As depicted, the distal portion 358 may be substantially linear or straight. In certain embodiments, the distal portion 358 may be curved, for example, the distal portion 358 may curve through a substantially circular arc. In certain other embodiments, only a portion of the distal portion 358 may be curved.

Additionally, as discussed above regarding the elongate members 104, 204, the elongate member 344 may be longitudinally openable and/or separable. In some other embodiments, the elongate member 344 may not be longitudinally openable or separable. Furthermore, in some embodiments the lateral vein introducer 342 may comprise reinforcement members analogous to the reinforcement members 101' of FIG. 1C.

Figure 7:
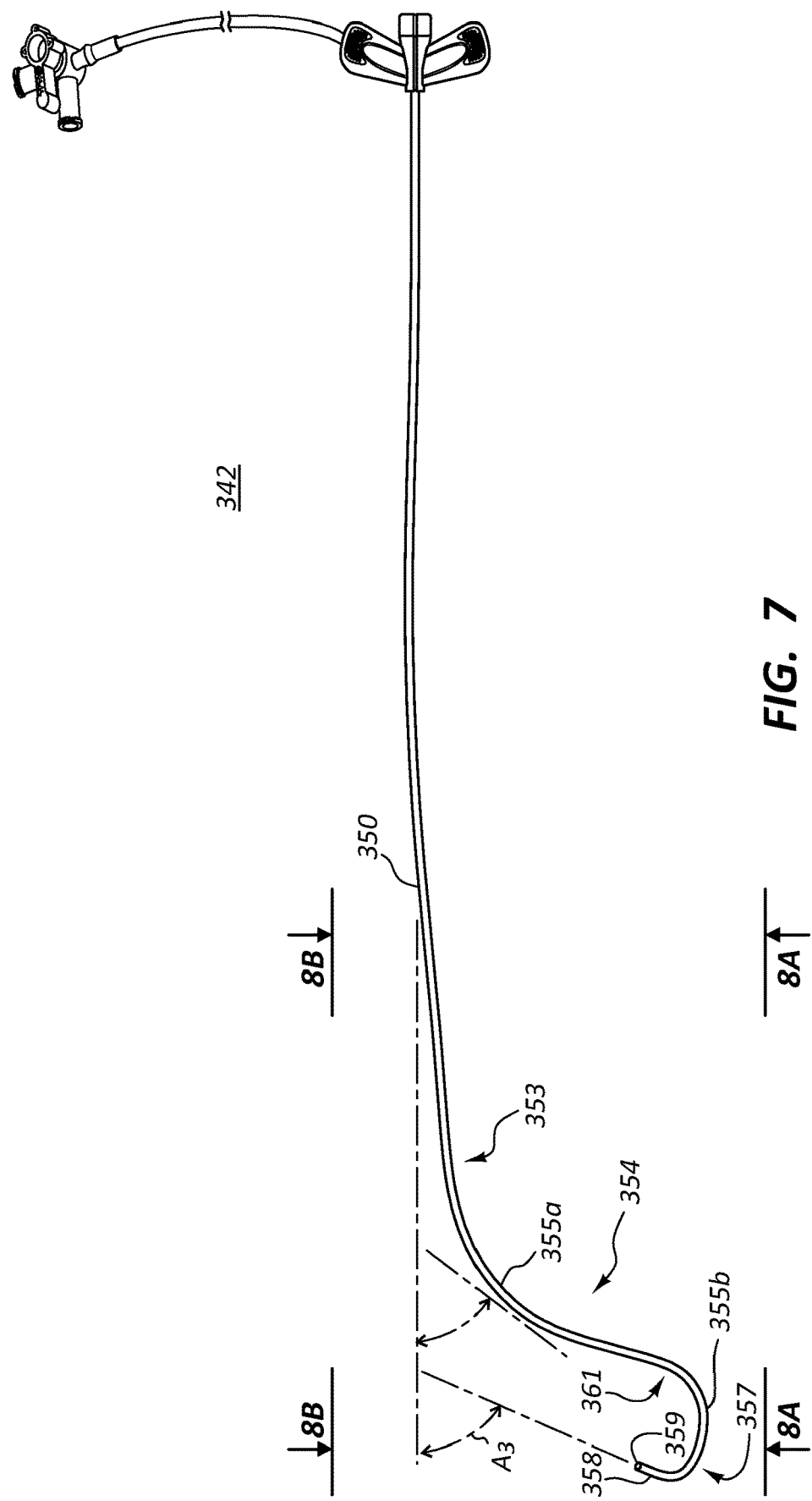
FIG. 7 is a top view of the lateral vein introducer of FIG. 6.

FIG. 7 is a top view of the lateral vein introducer 342 of FIG. 6. As depicted, a first transition portion 353 may be disposed or extend between each of the proximal portion 350 and the S-shaped portion 354. Similarly, a second transition portion 357 may be disposed or extend between each of the S-shaped portion 354 and the distal portion 358. Similarly, a third transition portion 361 may be disposed or extend between each of the first subportion 355a and the second subportion 355b of the S-shaped portion 354. In some embodiments, the first transition portion 353, the second transition portion 357, and/or the third transition portion 361 may be curved. For example, the first transition portion 353, the second transition portion 357, and/or the third transition portion 361 may curve through substantially circular arcs. The first transition portion 353, the second transition portion 357, and/or the third transition portion 361 may provide substantially smooth transitions between portions and/or subportions of the elongate member 344. Additionally, the radii of curvature of each of the first transition portion 353, the second transition portion 357, and the third transition portion 361 may be different. In some embodiments, the radii of curvature of each of the first transition portion 353, the second transition portion 357, and the third transition portion 361 may be substantially equal. Other combinations of radii of curvature of the first transition portion 353, the second transition portion 357, and the third transition portion 361 are also within the scope of this disclosure.

As depicted, an angle $A_3$ between a longitudinal axis of the proximal portion 350 where the proximal portion 350 meets the first subportion 355a and a longitudinal axis of the distal portion 358 at the distal tip 359 of the elongate member 344 may be less than 90°. In some embodiments, the angle between the longitudinal axis of the proximal portion 350 where the proximal portion 350 meets the first subportion 355a and a longitudinal axis of the distal portion 358 at a distal tip 359 of the elongate member 344 may be substantially equal to or greater than 90°.

In various embodiments, the length of the proximal portion 350 (i.e., along the longitudinal axis of the proximal portion 350) may be greater than the length of the S-shaped portion 354 (i.e., along the longitudinal axis of the S-shaped portion 354). Furthermore, the length of the S-shaped portion 354 may be greater than the length of the distal portion 358 (i.e., along the longitudinal axis of the distal portion 358). In various other embodiments, the length of the proximal portion 350 may be less than or substantially equal to the length of the S-shaped portion 354. Likewise, the length of the S-shaped portion 354 may be less than or substantially equal to the length of the distal portion 358. The length of the first subportion 355a (i.e., along the longitudinal axis of the first subportion 355a) may be substantially equal to the length of the second subportion 355b (i.e., along the longitudinal axis of the first subportion 355b). In some embodiments, the length of the first subportion 355a may be greater than the length of the second subportion 355b, or vice versa. Other combinations of the lengths of the proximal portion 350, the S-shaped portion 354, the first subportion 355a, the second subportion 355b, and/or the distal portion 358 are also within the scope of this disclosure.

In certain embodiments, the length of the proximal portion 350 may be at least about 35 cm. In certain other embodiments, the length of the proximal portion 350 may be between about 30 cm and about 60 cm, between about 35 cm and about 55 cm, between about 40 cm and about 50 cm, or another suitable length. The length of the S-shaped portion 354 may be between about 9 cm and about 25 cm, between about 12 cm and about 22 cm, between about 15 cm and about 19 cm, or another suitable length. The length of the first subportion 355a may be between about 5 cm and about 20 cm, between about 7 cm and about 15 cm, between about 9 cm and about 13 cm, or another suitable length. The length of the second subportion 355b may be between about 1.5 cm and about 15 cm, between about 2.5 cm and about 10 cm, between about 4 cm and about 8 cm, or another suitable length. Furthermore, the length of the distal portion 358 may be between about 0.1 cm and about 4 cm, between about 0.25 cm and about 2.5 cm, between about 0.5 cm and about 1.5 cm, or another suitable length.

FIG. 8A is a first side view of a portion of the lateral vein introducer 342 of FIG. 7. FIG. 8B is a second side view of the portion of the lateral vein introducer 342, which is opposite of the first side view. As depicted, the elongate member 344 is substantially disposed in a first plane. For example, each of the proximal portion 350, the S-shaped portion 354, and the distal portion 358 can be disposed in the first plane. In some other embodiments, various components of the lateral vein introducer 342 may be disposed in different planes when the lateral vein introducer 342 is disposed in an unconstrained configuration (i.e., when the elongate member 344 is not disposed within a subject's vasculature and/or is disposed on a flat surface). Analogous to the coronary sinus guides 102, 202, the lateral vein introducer 342 may also be flexible and upon disposition of a portion of the lateral vein introducer 342 within a vasculature of a subject, one or more portions of the lateral vein introducer 342 may conform to the three-dimensional shape of the vasculature.

As discussed above regarding the first core 172, the second core 392 may also be torqueable. Stated another way, while the second core 392 may be laterally flexible the second core 392 may also be torsionally stiff. In contrast, the lateral vein introducer 342 may be both laterally and torsionally flexible. The stiffness of the second core 392 may be enhanced by: increasing the thickness of the material forming the second core 392; forming the second core 392 from a stiff material; and/or disposing a reinforcement member such as a braid (e.g., a metal or fibrous braid) or one or more wires (e.g., nitinol wires) within a portion of the second core 392. The reinforcement member may enhance pushability and/or torqueability of the second core 392. In some embodiments, a braided reinforcement and/or a wire reinforcement may run along a length of the second core 392.

Furthermore, the second core 392 may be disposable within or configured to be disposed within the lumen 345 of the lateral vein introducer 342. Such a coupling of the second core 392 and the lateral vein introducer 342 may render the combination of the second core 392 and the lateral vein introducer 342 torqueable (wherein the lateral vein introducer 342 alone may not be substantially torqueable). In some embodiments, the second core 392 and the lateral vein introducer 342 may be coupled by: frictional engagement between an outer surface of the second core 392 and an inner surface of the lumen 345 of the lateral vein introducer 342; coupling together of the hub 366 of the lateral vein introducer 342 with the hub 393 of the second core 392; and/or an interference fit between the second core 392 and a similarly shaped lateral vein introducer 342. Such a coupling may permit or allow the distal end 348 of the lateral vein introducer 342 to be rotated when a proximal end 396 of the second core 392 is rotated.

The components of the coronary sinus access systems and the lateral vein delivery systems of the present disclosure are scalable. For example, although the shapes and/or sizes of various embodiments are specified herein, it is also to be expressly understood that these shapes and/or sizes may be scaled up or down from the illustrated embodiments given. For example, each of the recited dimensions may be specified as set forth above or increased or decreased by any percentage as may be desired according to the present disclosure. The components of the coronary sinus access systems and/or the lateral vein delivery systems may be adapted for hearts of similar topology but different sizes (e.g., for a child versus an adult).

Figure 9A:
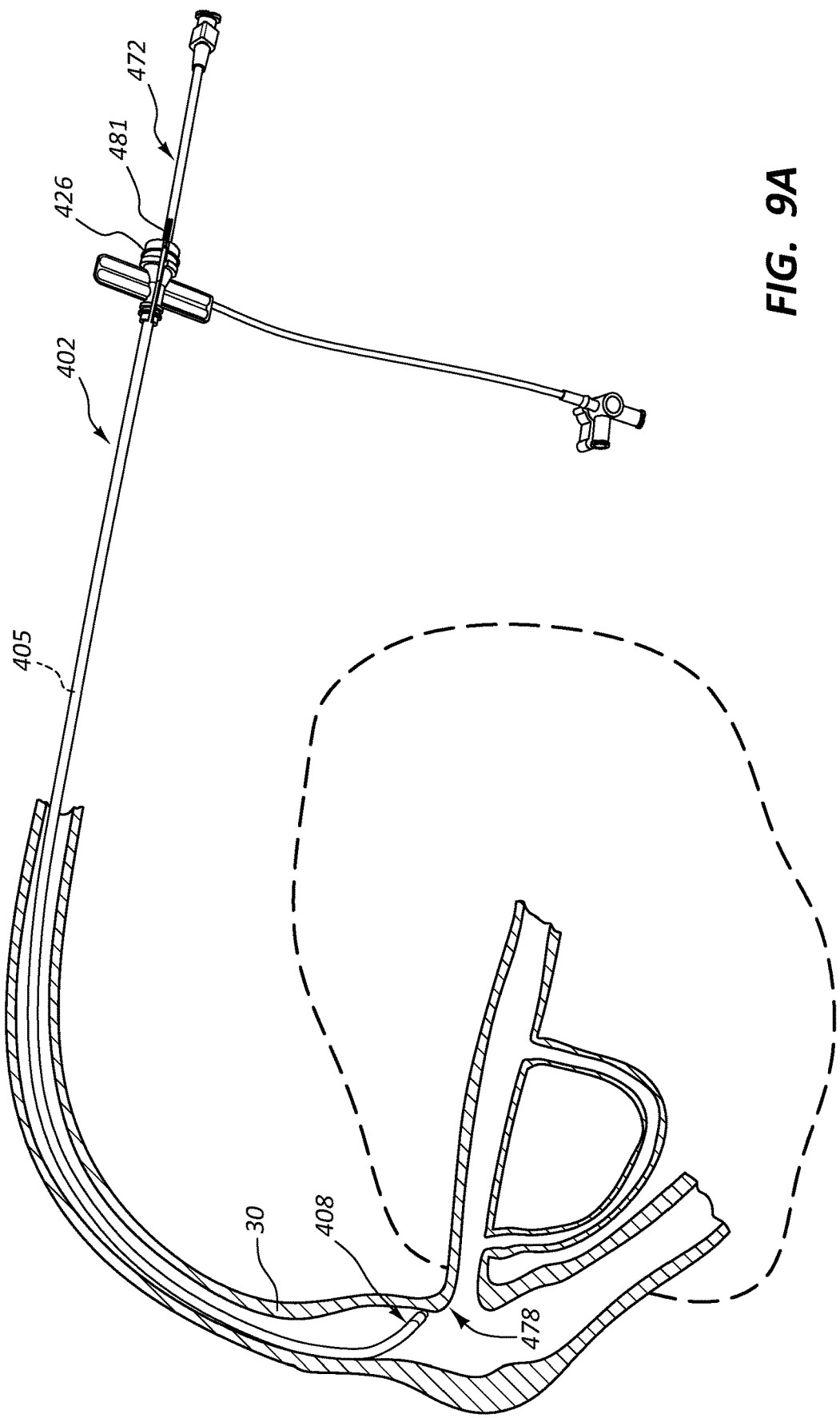
FIG. 9A depicts the disposition of a portion of a coronary sinus guide within a vessel of a subject.

Methods of using the coronary sinus access systems (e.g., coronary sinus access systems 100) and lateral vein delivery systems (e.g., lateral vein delivery system 340) are also disclosed herein. FIGS. 9A-9E depict an embodiment of a method of accessing a predetermined position within a vasculature of a subject. FIG. 9A illustrates the disposition of a portion of a coronary sinus guide 402 within a vessel 30 of a subject. Upon disposition of the coronary sinus guide 402 within a portion of the vessel 30, a first core 472 may be disposed within a lumen 405 of the coronary sinus guide 402.

The first core 472 may be disposed within the coronary sinus guide 402 such that a distal end 478 of the first core 472 extends distally in relation to a distal end 408 of the coronary sinus guide 402. A marker band 481 may be disposed on a portion of an external surface of the first core 472, such that when the marker band 481 is disposed adjacent a hub 426 of the coronary sinus guide 402, the marker band 481 may be configured to indicate to a practitioner that the distal end 478 of the first core 472 is extending distally in relation to the distal end 408 of the coronary sinus guide 402.

In some embodiments, the shape of the first core 472 may be substantially similar to the shape of the coronary sinus guide 402 such that upon disposition of the first core 472 within the lumen 405 of the coronary sinus guide 402 an interference fit, as discussed above, may be formed between the first core 472 and the coronary sinus guide 402. Furthermore, the first core 472 may be stiffer and more torqueable than the coronary sinus guide 402 such that the first core 472 may aid in disposition of the coronary sinus guide 402 within the vasculature of the subject. For example, as depicted in FIG. 9B, the first core 472 may aid in guiding or steering the coronary sinus guide 402 through the tortuous vasculature of the subject.

Figure 9C:
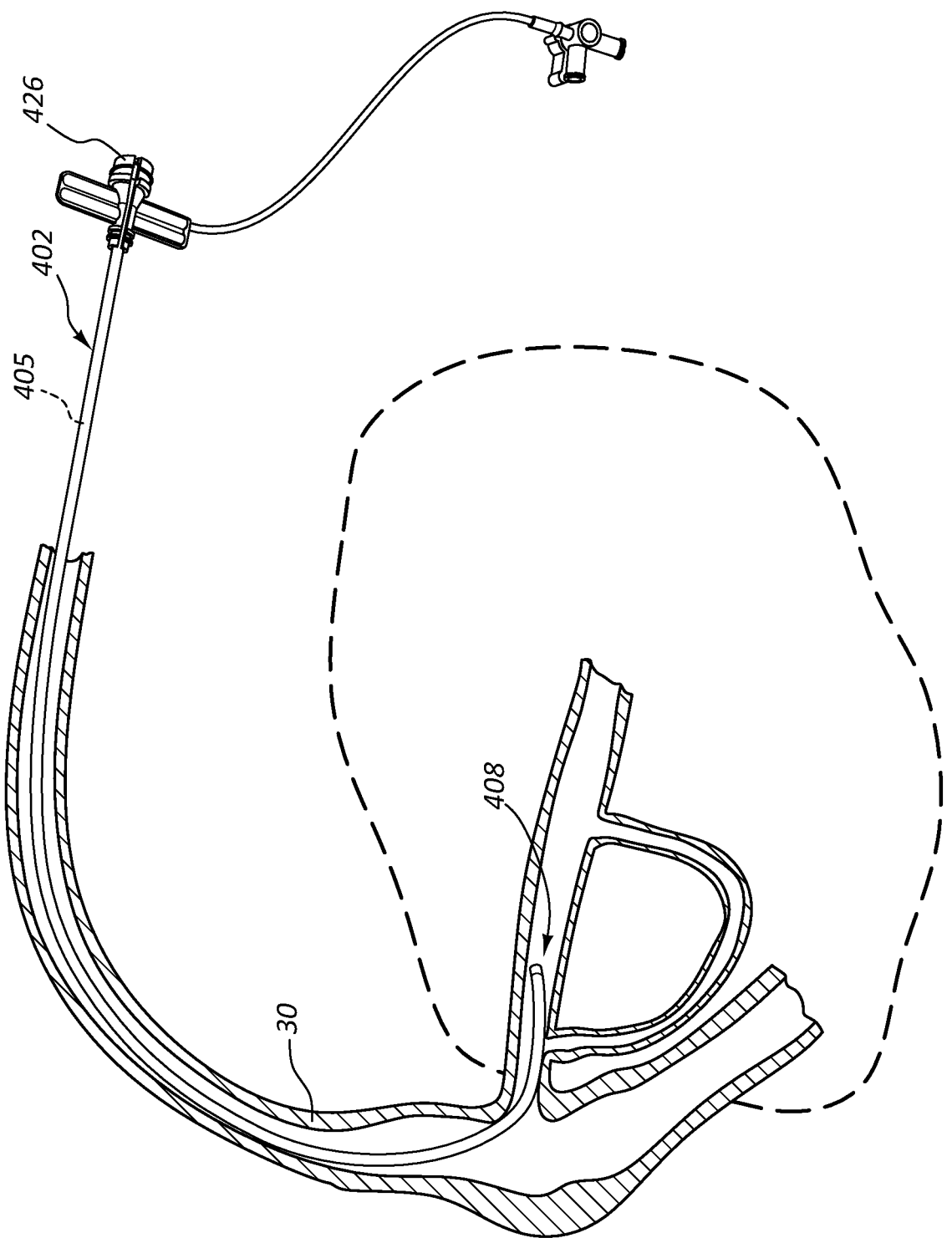
FIG. 9C depicts removal of the first core of FIG. 9B from a lumen of the coronary sinus guide.
Figure 9D:
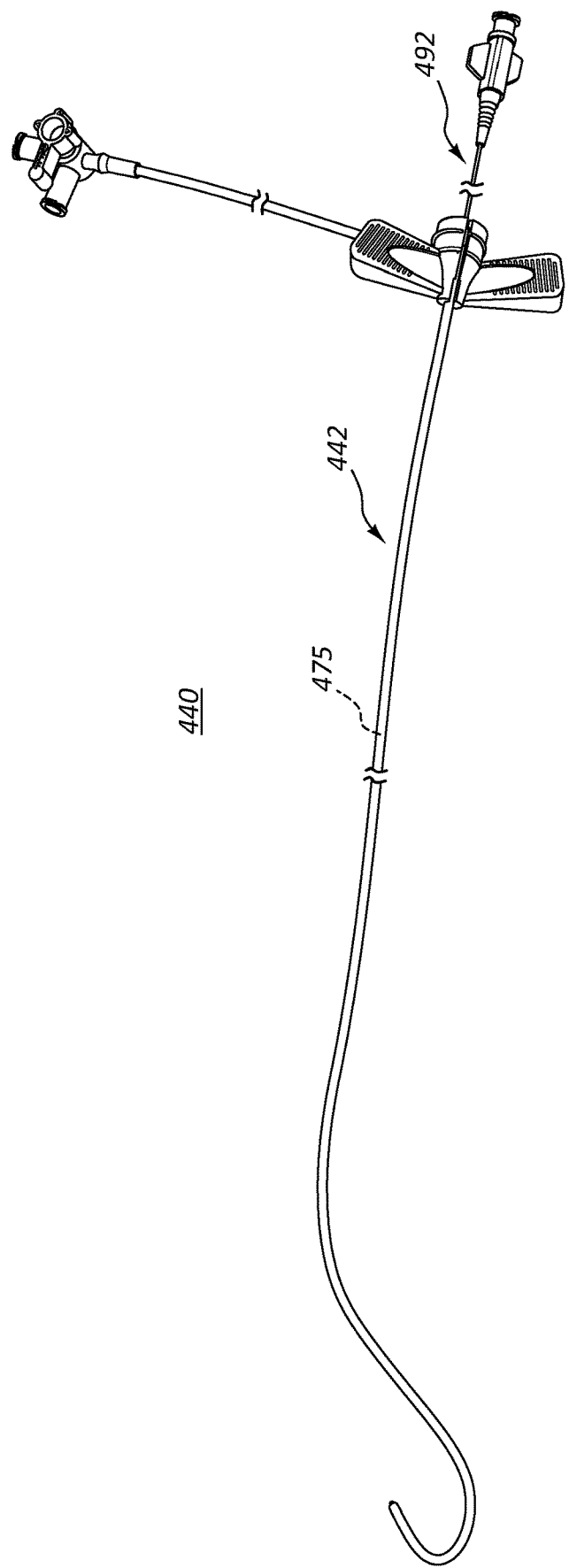
FIG. 9D depicts a lateral vein delivery system.
Figure 9E:
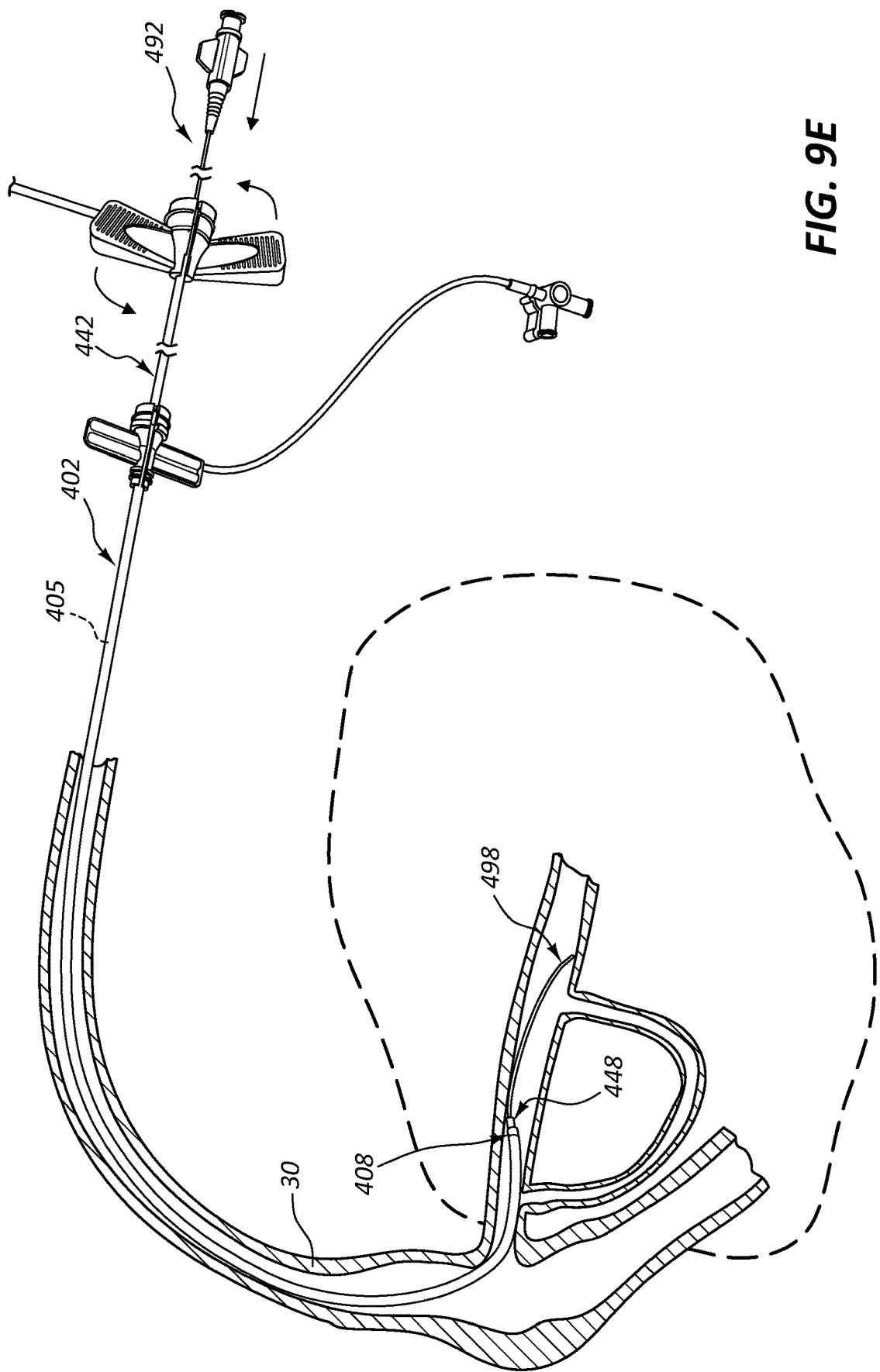
FIG. 9E depicts disposition of a lateral vein introducer and a second core within the lumen of the coronary sinus guide.

In some embodiments, once the distal end 408 of the coronary sinus guide 402 has been disposed at a desired position within the vasculature of the subject, the first core 472 may be removed from the lumen 405 of the coronary sinus guide 402 (see FIG. 9C). In certain embodiments, the practitioner may obtain a lateral vein delivery system 440, including a lateral vein introducer 442 and a second core 492, as shown in FIG. 9D. While the lateral vein introducer 442 may be compressible, flexible, or pliable, the second core 492 may be stiff and torqueable. In certain embodiments, the second core 492 may be disposed within a lumen 475 of the lateral vein introducer 442. As discussed above regarding the coronary sinus guide 402 and the first core 472, an interference fit may also be formed between the second core 492 and the lateral vein introducer 442 such that the second core 492 may aid in guiding or steering the lateral vein introducer 442 through a portion of the vasculature of the subject. With reference to FIG. 9E, the lateral vein introducer 442 and the second core 492 may then be disposed within the lumen 405 of the coronary sinus guide 402. A distal end 498 of the second core 492 may be extended distally in relation to the distal end 408 of the coronary sinus guide 402 and a distal end 448 of the lateral vein introducer 442. Furthermore, the second core 492 may aid in locating a desired vein or position within the vasculature of the subject. As can be appreciated, additional methods and/or method steps can be derived from FIGS. 1A-9E and the corresponding disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A coronary access system, comprising:
   a coronary sinus access system, comprising:
     a coronary sinus guide, comprising:
       an elongate member including a proximal end and a distal end, wherein the elongate member comprises:
         a proximal portion;
         a curved medial portion extending distally from the proximal portion, the curved medial portion curving through a substantially circular arc, the proximal portion and the medial portion disposed in a first plane; and
         a distal portion extending distally from the curved medial portion in a second plane, wherein the distal end of the elongate member is directed in a proximal direction; and
       a first core member disposable within the elongate member, wherein the first core member comprises a nitinol reinforcement member; and
   a lateral vein delivery system, comprising:
     a lateral vein introducer; and
     a second core member disposable within the lateral vein introducer, wherein the second core member comprises a nitinol reinforcement member.

2. The coronary access system of claim 1, wherein the proximal portion is curved.

3. The coronary access system of claim 1, wherein the substantially circular arc is defined by a chord having a length and wherein the curved medial portion has a height above the chord.

4. The coronary access system of claim 3, wherein the chord extends between a longitudinal axis of the elongate member at a junction of the proximal portion and the curved medial portion and the longitudinal axis of the elongate member at a junction of the curved medial portion and the distal portion.

5. The coronary access system of claim 4, wherein the length of the chord is between about 10 cm and about 20 cm.

6. The coronary access system of claim 4, wherein the height above the chord is between about 2 cm and about 8 cm.

7. The coronary access system of claim 1, wherein a length of the proximal portion is greater than a length of the curved medial portion, and wherein the length of the curved medial portion is greater than a length of the distal portion.

8. The coronary access system of claim 1, wherein a length of the proximal portion is at least about 15 cm.

9. The coronary access system of claim 1, wherein a length of the curved medial portion is between about 15 cm and about 25 cm.

10. The coronary access system of claim 1, wherein a length of the distal portion is between about 1 cm and about 5 cm.

11. The coronary access system of claim 1, wherein a dihedral angle between the first plane and the second plane is between about 10° and about 30°.

12. The coronary access system of claim 1, wherein the elongate member comprises a nitinol reinforcement member extending longitudinally along a portion of the elongate member.

13. A coronary access system comprising:
   a coronary sinus access system, comprising:
     a coronary sinus guide; and
     a first core member disposable within the coronary sinus guide; and
   a lateral vein delivery system, comprising:
     a lateral vein introducer, comprising:

an elongate member including a proximal end and a distal end, wherein the elongate member comprises:
a proximal portion;
an S-shaped portion extending distally from the proximal portion, wherein the S-shaped portion comprises:
a proximal subportion curving through a first arc; and
a distal subportion extending distally from the proximal subportion, the distal subportion curving through a second arc; and
a distal portion extending distally from the S-shaped portion;
and
a second core member disposable within the elongate member, wherein the second core member comprises a nitinol reinforcement member.

14. The coronary access system of claim 13, wherein the proximal portion, the S-shaped portion, and the distal portion are disposed in a first plane.

15. The coronary access system of claim 13, wherein a radius of curvature of the first arc is greater than a radius of curvature of the second arc.

16. The coronary access system of claim 13, wherein a longitudinal axis of the distal portion is substantially straight.

17. The coronary access system of claim 13, wherein an angle between a longitudinal axis of the proximal portion where the proximal portion meets the proximal subportion and a longitudinal axis of the distal portion at a distal tip of the elongate member is less than 90°.

18. The coronary access system of claim 13, wherein the elongate member comprises a lumen extending between the proximal end and the distal end.

19. The coronary access system of claim 1, wherein the first core further comprises:
an elongate member including a proximal portion; a curved medial portion extending distally from the proximal portion, the proximal portion and the medial portion disposed in a first plane; and a distal portion extending distally from the curved medial portion in a second plane; and
wherein the coronary sinus guide comprises, a lumen configured to receive the first core, wherein a shape of the first core is substantially similar to a shape of the coronary sinus guide, such that upon disposition of the first core within the coronary sinus guide an interference fit is formed.

20. The coronary sinus access system of claim 19, wherein the first core is stiffer than the coronary sinus guide, such that the first core is torqueable, and wherein upon formation of the interference fit between the first core and the coronary sinus guide, rotation of a proximal end of the first core is configured to rotate a distal end of the first core and the distal end of the coronary sinus guide.

21. A coronary access assembly, comprising:
a coronary sinus access system comprising:
a coronary sinus guide comprising:
a first elongate member including a proximal end and a distal end, wherein the first elongate member comprises:
a proximal portion;
a curved medial portion extending distally from the proximal portion, the curved medial portion curving through a substantially circular arc, the proximal portion and the medial portion disposed in a first plane; and
a distal portion extending distally from the curved medial portion in a second plane, wherein the distal end of the first elongate member is directed in a proximal direction; and
a first core member disposable within the coronary sinus guide, wherein the first core member comprises a nitinol reinforcement member; and
a lateral vein delivery system comprising:
a lateral vein introducer, comprising:
a second elongate member including a proximal end and a distal end, wherein the second elongate member comprises:
a proximal portion;
an S-shaped portion extending distally from the proximal portion; and
a distal portion extending distally from the S-shaped portion; and
a second core member disposable within the coronary sinus guide, wherein the second core member comprises a nitinol reinforcement member.

* * * * *